United States Patent [19]

Scherer et al.

[11] Patent Number: 4,745,798
[45] Date of Patent: May 24, 1988

[54] METHOD AND DEVICE FOR MEASURING PARAMETERS IN A SUSPENSION

[75] Inventors: Hans-Joachim Scherer, Mainbernheim; Andreas Gazinski, Veitschochheim, both of Fed. Rep. of Germany

[73] Assignee: KRC Umwelttechnik GmbH, Wurzburg, Fed. Rep. of Germany

[21] Appl. No.: 30,234

[22] Filed: Mar. 26, 1987

[30] Foreign Application Priority Data

Mar. 29, 1986 [DE] Fed. Rep. of Germany ....... 3610739

[51] Int. Cl.$^4$ ............................................. G01N 15/00
[52] U.S. Cl. ................................. 73/61 R; 210/512.1
[58] Field of Search ...................... 73/61 R, 61.4, 63; 210/512.1; 209/211

[56] References Cited

U.S. PATENT DOCUMENTS

| | | | |
|---|---|---|---|
| 3,334,516 | 8/1967 | Cedrone | 73/61 R |
| 4,216,095 | 8/1980 | Ruff | 210/512.1 |
| 4,343,707 | 8/1982 | Lucas | 210/512.1 |
| 4,397,741 | 8/1983 | Miller | 210/512.1 X |

Primary Examiner—Stewart J. Levy
Assistant Examiner—Joseph W. Roskos
Attorney, Agent, or Firm—Wegner & Bretschneider

[57] ABSTRACT

A method for measuring parameters in suspensions containing particles which have a specific gravity greater than the liquid, by means of measuring probes in the interior of a quiescent-flow vessel. The method includes tangentially introducing a stream of the suspension into the flow vessel at one end thereof and tangentially withdrawing it therefrom at the other end thereof, under the same direction of rotation. The device is adapted for measuring a descending or an ascending stream, whereby, for measuring an ascending stream, the diameter at the top of the vessel is larger than the diameter at the bottom.

8 Claims, 1 Drawing Sheet

METHOD AND DEVICE FOR MEASURING PARAMETERS IN A SUSPENSION

TECHNICAL FIELD OF THE INVENTION

The present invention relates to a method and to a device for measuring parameters of suspensions of particles which have a specific gravity greater than that of the liquid, by means of measuring probes in the interior of a vessel through which quiescent liquid flows.

BACKGROUND OF THE INVENTION

In chemical process technology, it is necessary to continuously or intermittently measure a number of parameters. Such parameters include, for example, the pH value, the redox potential, the conductivity, the contents of free or dissolved oxygen and the concentrations of other components dissolved in the liquid. The measurement of these parameters in suspensions always involves some difficulties and these difficulties may increase in the case that the suspensions contain contaminating, sticking or crystallizing components. Rapidly agitated suspensions cause abrasion to the equipment and erroneous measurements may be obtained on the measuring probes.

Typically, prior art devices attempt to alleviate the above problems by passing a portion of the suspension through a quiescent-flow vessel, having probes therein for measuirng the desired parameters. However, there is a drawback with such devices, in that they clog relatively easily and have to be replaced or cleaned rather often.

SUMMARY OF THE INVENTION

It is an object of the present invention to provide a method and a device by means of which parameters may be measured, continuously or intermittently, in suspensions of particles which have a higher specific gravity than the liquid, while, at the same time, no clogging, sticking or other impairments occur in the flow vessel or at the measuring probes. In one preferred embodiment of the invention, there is no need to use any mechanical cleaning devices, as these create severe sealing problems which are resolvable only at high expenses.

Surprisingly, the object of the present invention can easily and simply be attained by introducing the stream to be measured tangentially into the vessel at one end thereof and tangentially withdrawing the suspension therefrom at the other end, under the same direction of rotation. This causes an even, non-turbulent, rotational motion of the fluid within the vessel to occur and the specifically heavier suspended particles helically pass through the flow vessel. This leads to a permanent self-cleaning of the vessel and prevents any deposition, plugging or other difficulties. The measuring probes can be positioned in the interior, and preferably even in the center, of the vessel. The center of the vessel is a particularly quiescent-flow zone and probes thus positioned would not be subject to any damaging abrasion.

DETAILED DESCRIPTION OF THE PREFERRED EMBODIMENTS

Figure 1:
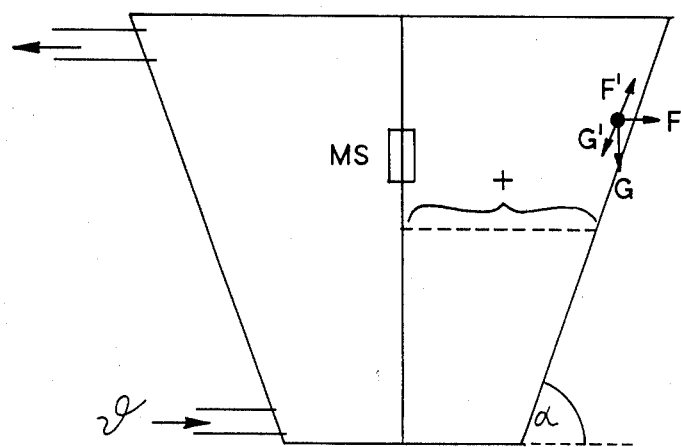
FIG. 1 is a schematic view of a quiescent-flow vessel in accordance with a preferred embodiment of the present invention.

A preferred embodiment of the method according to the present invention uses a descending stream in which the angular velocity of the rotating suspension remains constant or decreases from the top to the bottom. This is accomplished by a design in which the diameter of the top of the flow vessel is smaller than or equal to the diameter of the bottom of the flow vessel.

However, it is preferred to measure in an ascending stream, because, after the desired continuous or intermittent measurements have been taken, the flow vessel is rinsed by the suspension with its heaviest particles removed, as will be further explained below, and the vessel is then immediately available for further measurements.

For carrying out the method of measuring in an ascending stream, according to the present invention, it is necessary that the angular velocity of the rotating suspension be decreased from the bottom to the top. This is accomplished by a design, illustrated in FIG. 1, in which the diameter of the vessel is larger near the top of the vessel than it is near the bottom of the vessel.

In the preferred embodiment of FIG. 1, a vessel 10 is shown, having a measuring probe 16, wherein:
F = the centrifugal force;
G = the weight force;
F′ = the centrifugal force component and
G′ = the gravitational component of a particle in the suspension.

Input 12 and output 14 are both tengential to the rotational flow path within the vessel. Of course, the measuring probe may be connected to suitable displays or processor means.

Particularly good results are obtained, if the centrifugal force component acting on the particles of the suspension which have the greatest specific gravity is greater than the gravitational component, i.e., if F′ > G′. This state is realized with a design in which the inclination angle to the horizontal of the side wall $\alpha$ is smaller than arctan $rg/\theta^2$ wherein
r is the average radius of the vessel,
g is the gravitation of the specifically heaviest particles of the suspension, and
$\theta$ is the flow velocity parameter.

By having the vessel being shaped as a truncated cone, as in a centrifuge, the particles of the suspension with the greatest specific gravity first migrate to the wall and, having arrived there, are more rapidly advanced upwardly than the rest of the suspension. Thus, the largest and heaviest particles migrate faster upwardly from the bottom to the top. Once the heaviest particles migrate to the top, they are removed, and the remaining suspension "rinses" the vessel, as previously discussed.

The method according to the invention and the device for carrying out the invention have been tested in measuring the pH in washing suspensions of flue gas washing which are operated using limestone as an absorbing agent and wherefrom calcium sulfate dihydrate (gypsum) is precipitated. Previously, the pH value was measured in a cylindrical pot with centrally arranged electrodes, an inlet formed as an extension of the pot radius and an outlet disposed centrally downwardly. In such measuring pots, after some time, deposition of a limestone suspension and of crystallizing gypsum took place, so that malfunctions of the equipment and error in measurements occurred. In contrast thereto, a device in accordance with the present invention operated trouble-free for months and, upon occasional checks, showed that the interior of the vessel remained entirely clean and free from deposits. The measuring probe was not exposed to any visible abrasion in the highly-quiescent flow region in the center of the flow vessel. Since the device according to the invention contains virtually no moving or abrasion-subjected parts, it is suitable to be used for continuous or intermittent measurements over long periods of time. In the case of intermittent measurements, after the measurement has been completed, the vessel may be flushed with the suspension, without the heavier particles, or with a cleaning fluid, and then without delay is available for each new measurement. It will be clear that the same good results may also be expected for measuring other parameters in other suspensions.

The foregoing description is for illustrative purposes only. Modifications may be made, within the scope of the invention, as defined by the broad, general meaning of the terms in which the appended claims are expressed.

What is claimed is:

1. Method for measuring parameters in suspensions containing particles having a specific gravity greater than the liquid comprising:
   tangentially introducing a stream of the suspension to be measured into a quiescent-flow vessel at one end thereof;
   tangentially withdrawing said stream at the other end of the vessel so that a smooth rotational flow of the suspension is created within said vessel; and
   sensing a parameter of the suspension by means of at least one measuring probe located in the interior of the quiescent-flow vessel.

2. Method according to claim 1, wherein said stream is a descending stream and the angular velocity of said rotating suspension remains constant or decreases from the top to the bottom.

3. The method according to claim 1, wherein said stream is an ascending stream and the angular velocity of the rotating suspension is decreased from the bottom to the top.

4. The method according to claim 3, wherein the centrifugal force component of the heaviest particles of the suspension is greater than the gravitational component.

5. Device for continuously measuring parameters in suspensions containing particles which have a specific gravity greater than the liquid comprising:
   a quiescent-flow vessel comprising a tangential inlet opening at one end of said vessel for introducing a stream of said suspension into said vessel and a tangential output for withdrawing said suspension from said vesesl, said suspension flowing in a smooth, rotational flow within said vessel; and
   measuring means in the interior of the quiescent-flow vessel for sensing a parameter of the suspension by means of at least one measuring probe.

6. The device according to claim 5, wherein said suspension is a descending stream and the diameter at the top of said vessel is smaller than or equal to the diameter at the bottom.

7. The device according to claim 5, wherein said suspension is an ascending stream and the diameter at the top of said vessel is larger than the diameter at the bottom.

8. The device according to claim 7, wherein the inclination angle $\alpha$, with respect to the horizontal, of the side wall of said vessel is smaller than arctan $rg/\theta^2$ wherein
   r is the average radius of the vessel,
   g is the gravitation of the specifically heaviest particles of the suspension, and
   $\theta$ is the flow velocity parameter.

* * * * *